United States Patent
Gill et al.

(10) Patent No.: US 9,463,073 B2
(45) Date of Patent: Oct. 11, 2016

(54) METHOD AND APPARATUS FOR ANALYSING IMAGES

(75) Inventors: Steven Streatfield Gill, Bristol (GB); Jian-Kun Shen, Wotton-under-Edge (GB)

(73) Assignee: RENISHAW (IRELAND) LIMITED, Swords (IE)

( * ) Notice: Subject to any disclaimer, the term of this patent is extended or adjusted under 35 U.S.C. 154(b) by 408 days.

(21) Appl. No.: 13/994,459

(22) PCT Filed: Dec. 21, 2011

(86) PCT No.: PCT/GB2011/001754
§ 371 (c)(1),
(2), (4) Date: Jun. 14, 2013

(87) PCT Pub. No.: WO2012/085511
PCT Pub. Date: Jun. 28, 2012

(65) Prior Publication Data
US 2013/0279784 A1    Oct. 24, 2013

(30) Foreign Application Priority Data

Dec. 21, 2010   (EP) .................................. 10252178

(51) Int. Cl.
*G06K 9/00* (2006.01)
*A61B 19/00* (2006.01)
(Continued)

(52) U.S. Cl.
CPC ........... *A61B 19/5244* (2013.01); *A61B 6/032* (2013.01); *A61B 6/501* (2013.01);
(Continued)

(58) Field of Classification Search
None
See application file for complete search history.

(56) References Cited

U.S. PATENT DOCUMENTS 5,961,454 A    10/1999   Kooy et al.
6,349,245 B1   2/2002    Finlay
(Continued)

FOREIGN PATENT DOCUMENTS

CN    1910616 A         2/2007
JP    2007-531553 A    11/2007
(Continued)

OTHER PUBLICATIONS

Koos, W. T., K. Roessler, and C. Matula. "Image-guided neurosurgery with intra-operative CT." (1998).*
(Continued)

*Primary Examiner* — Nirav G Patel
(74) *Attorney, Agent, or Firm* — Oliff PLC (57) ABSTRACT

A method is described for determining brain shift, such as the brain shift that occurs following a neurosurgical intervention. The method includes taking a first image of the brain of a subject, the first image showing the position of blood vessels in the brain relative to a reference position. A second image of the brain that has been acquired following an intervention on the subject is also taken. This second image has been acquired using computed tomography imaging apparatus. The second image shows the position of blood vessels in the brain relative to the reference position. Brain shift is then determined from the shift in position of the blood vessels in at least one region of interest of the brain, with respect to the reference position, between the first and second images. Corresponding apparatus is also described.

15 Claims, 6 Drawing Sheets

(51) Int. Cl.
| | |
|---|---|
| *G06T 7/00* | (2006.01) |
| *A61B 6/03* | (2006.01) |
| *A61G 13/00* | (2006.01) |
| *A61B 6/00* | (2006.01) |
| *A61B 17/00* | (2006.01) |

(52) U.S. Cl.
CPC .............. *A61B 34/20* (2016.02); *A61B 34/30* (2016.02); *A61B 90/37* (2016.02); *A61B 90/39* (2016.02); *A61G 13/00* (2013.01); *G06T 7/003* (2013.01); *G06T 7/0014* (2013.01); *G06T 7/0044* (2013.01); *A61B2017/00694* (2013.01); *A61B 2034/107* (2016.02); *A61B 2034/2065* (2016.02); *A61B 2034/303* (2016.02); *A61B 2090/363* (2016.02); *A61B 2090/364* (2016.02); *A61B 2090/374* (2016.02); *A61B 2090/3762* (2016.02); *A61B 2090/3966* (2016.02); *A61B 2090/3983* (2016.02); *G06T 2200/04* (2013.01); *G06T 2207/10081* (2013.01); *G06T 2207/30016* (2013.01); *G06T 2207/30101* (2013.01); *G06T 2210/41* (2013.01)

(56) References Cited

U.S. PATENT DOCUMENTS

| | | |
|---|---|---|
| 6,351,513 B1 | 2/2002 | Bani-Hashemi et al. |
| 6,389,104 B1 | 5/2002 | Bani-Hashemi et al. |
| 7,072,705 B2 | 7/2006 | Miga et al. |
| 7,225,012 B1 | 5/2007 | Susil et al. |
| 7,570,791 B2 | 8/2009 | Frank et al. |
| 7,587,076 B2 | 9/2009 | Kraus et al. |
| 8,010,177 B2 | 8/2011 | Csavoy et al. |
| 8,036,441 B2 | 10/2011 | Frank et al. |
| 8,041,089 B2 | 10/2011 | Drumm et al. |
| 8,060,181 B2 | 11/2011 | Rodriguez Ponce et al. |
| 8,218,843 B2 | 7/2012 | Edlauer et al. |
| 8,238,631 B2 | 8/2012 | Hartmann et al. |
| 8,472,691 B2 | 6/2013 | Furst |
| 8,503,745 B2 | 8/2013 | Simon et al. |
| 8,548,563 B2 | 10/2013 | Simon et al. |
| 8,705,829 B2 | 4/2014 | Frank et al. |
| 8,737,708 B2 | 5/2014 | Hartmann et al. |
| 2001/0036303 A1 | 11/2001 | Maurincomme et al. |
| 2003/0023154 A1 | 1/2003 | Nitz |
| 2004/0008028 A1 | 1/2004 | Horger et al. |
| 2005/0004454 A1 | 1/2005 | Mitschke et al. |
| 2005/0171558 A1 | 8/2005 | Abovitz et al. |
| 2005/0203420 A1 | 9/2005 | Kleen et al. |
| 2005/0267350 A1 | 12/2005 | McKinnon |
| 2006/0036167 A1 | 2/2006 | Shina |
| 2006/0235669 A1 | 10/2006 | Charbel et al. |
| 2006/0241465 A1 | 10/2006 | Huennekens et al. |
| 2006/0257006 A1 | 11/2006 | Bredno et al. |
| 2007/0021669 A1 | 1/2007 | Miga et al. |
| 2007/0123771 A1 | 5/2007 | Redel et al. |
| 2007/0127845 A1 | 6/2007 | Fu et al. |
| 2007/0225553 A1 | 9/2007 | Shahidi |
| 2007/0238961 A1 | 10/2007 | Vilsmeier et al. |
| 2007/0287905 A1 | 12/2007 | Klingenbeck-Regn |
| 2008/0199059 A1 | 8/2008 | Eck et al. |
| 2008/0212857 A1 | 9/2008 | Pfister et al. |
| 2008/0212858 A1 | 9/2008 | Boese et al. |
| 2008/0278492 A1 | 11/2008 | Ruijters et al. |
| 2009/0041301 A1 | 2/2009 | Finlay et al. |
| 2009/0093706 A1 | 4/2009 | Zhang et al. |
| 2009/0123046 A1* | 5/2009 | Mielekamp .......... A61B 6/4441 382/130 |
| 2009/0156927 A1 | 6/2009 | Schmidt |
| 2009/0177081 A1 | 7/2009 | Joskowicz et al. |
| 2009/0281417 A1 | 11/2009 | Hartmann et al. |
| 2010/0160771 A1 | 6/2010 | Gielen et al. |
| 2010/0290690 A1 | 11/2010 | Hartmann et al. |
| 2011/0257514 A1 | 10/2011 | Bucki et al. |
| 2012/0027261 A1 | 2/2012 | Frank et al. |
| 2012/0143048 A1 | 6/2012 | Finlay |
| 2012/0201421 A1 | 8/2012 | Hartmann et al. |
| 2014/0058747 A1 | 2/2014 | Thomson et al. |

FOREIGN PATENT DOCUMENTS

| | | |
|---|---|---|
| WO | WO 96/07144 A1 | 3/1996 |
| WO | WO 03/077784 A1 | 9/2003 |
| WO | WO 2005/025404 A2 | 3/2005 |
| WO | WO 2006/028474 A1 | 3/2006 |
| WO | WO 2006/075331 A2 | 7/2006 |
| WO | WO 2008/053165 A1 | 5/2008 |
| WO | WO 2008/059417 A1 | 5/2008 |
| WO | WO 2010/037850 A2 | 4/2010 |

OTHER PUBLICATIONS

Ohue, Shiro, et al. "Evaluation of intraoperative brain shift using an ultrasound-linked navigation system for brain tumor surgery." Neurologia medico-chirurgica 50.4 (2010): 291-300.*
Jun. 2, 2015 Office Action issued in Japanese Application No. 2013-545489.
May 19, 2015 Office Action issued in European Application No. 11 808 909.3.
Dec. 2, 2014 Office Action issued in Chinese Application No. 201180065112.X.
Bucki et al., "Framework for a Low-Cost Intra-Operative Image-Guided Neuronavigator Including Brain Shift Compensation," *Proceedings of the 29th Annual International Conference of the IEEE EMBS*, Aug. 23-26, 2007, pp. 872-875.
Renishaw W *Neuromate User Manual*, Sep. 2010, pp. 1-117.
Jul. 22, 2011 Partial European Search Report issued in European Patent Application No. EP 10 25 2178.
Mar. 28, 2012 Written Opinion of the International Searching Authority issued in International Application No. PCT/GB2011/001754.
Mar. 28, 2012 International Search Report issued in International Application No. PCT/GB2011/001754.
Sep. 6, 2015 Office Action issued in Chinese Patent Application No. 201180065112.
Reinertsen et al, Validation of Vessel-Based Registration for Correction of Brain Shift, ScienceDirect, Medical Image Analysis 11 (2007) pp. 374-388.
Reinertsen et al., "Vessel Driven Correction of Brain Shift", (2004).
Susil et al, "A Single Image Registration Method for CT Guided Interventions", Department of Biomedical Engineering, Department of Radiology, Department of Computer Science, The Johns Hopkins University, Baltimore, Maryland, Published in Medical Image Computing and Computer-Assisted Intervention, 1999.
Fichtinger et al., "Surgical and Interventional Robotics: Part II: Surgical CAD-CAM Systems", IEEE Robotics and Automation, Sep. 2008, pp. 1-8.
Feb. 9, 2016 Office Action Issued in U.S. Appl. No. 14/820,310.
Mar. 1, 2016 Office Action issued in Japanese Patent Application No. 2013-545489.
Jul. 21, 2016 Office Action Issued in U.S. Appl. No. 14/820,310.

* cited by examiner

METHOD AND APPARATUS FOR ANALYSING IMAGES

The present invention relates to an apparatus and method for analysing images of the brain and in particular to a computer implemented technique for determining brain shift from images of the brain in which blood vessels are visible.

A variety of neourosurgical techniques have been developed over the years that involve inserting neurosurgical instruments, such as catheters or electrodes, to targets within the brain parenchyma. These may be guided to a position with sub-millimeter accuracy using stereotactic techniques of the type described in, for example, EP1509153.

Although stereotactic apparatus is available that can precisely guide neurosurgical instruments to a predetermined location, there is no guarantee that such instruments actually reach the target structure within the brain that has been identified by the surgeon from pre-operative MRI scans or the like. For example, the accuracy with which a brain structure can be targeted may be affected by so-called "brain shift" that often occurs following the MRI scan that was used to identify the brain target. There are various reasons why such brain shift may occur. For example, it may arise from any changes in the orientation of the patient's head between image acquisition and placement on the operating table. Leakage of cerebrospinal fluid (CSF) and the ingress of air into the skull during surgery can also cause the brain to sink. Furthermore, there may be displacement or swelling of the brain within the skull as neurosurgical instruments are forced through the brain tissue.

To date, the existence of brain shift has been noted by surgeons and surgical procedures have been devised and adapted to minimise its effect. This has been attempted by, for example, always placing a patient's head in a certain orientation during surgery (although such an orientation may be sub-optimal for surgical access purposes) to minimise brain shift. Similarly, neurosurgeons often compensate for brain shift by adding an offset to the target position identified in an MRI image based on experience gained from previous surgical procedures about the magnitude of brain shift that is likely to occur. Although such known techniques can compensate for the effects of brain shift in most cases, they are highly subjective and rely totally on the skill and judgement of the neurosurgeon. The existence of brain shift also means it is typically not possible to tell if the desired target has been reached by an implanted neurosurgical instrument (e.g. electrode, catheter etc) during the surgical procedure itself; this is only established subsequently by a follow-up MRI scan.

Various techniques have been developed previously for image-guided neurosurgery that attempt to measure or predict brain shift. For example, WO2005/025404 describes a cortical surface registration technique. In particular, WO2005/025404 describes using a line stripe laser scanner to intra-operatively measure the three dimensional profile of the cortical surface. This surface profile is then registered to previously acquired MRI data. WO2010/037850 describes how brain shift may be estimated using a biomechanical model that analyses pre-operatively acquired MRI images and intra-operatively acquired Doppler ultrasound images. A biomechanical model for estimating brain shift is also described in the publication "Framework for a low-cost intra-operative image-guided neuronavigator including brain shift compensation" by M Bucki et al., 2007 Annual international conference of the IEEE engineering in medicine and biology society, Lyon, France, 22-26 Aug. 2007, pages 872-875 (ISBN:987-1-4244-0787-3). WO2006/028474 describes generating a statistical atlas of brain displacements using intra-operative images of the brain surface. None of these techniques, however, provide a sufficiently accurate and reliable measure of brain shift that can be used to assess and/or improve the accuracy of device placement in complex (e.g. deep brain) neurosurgical procedures.

According to the present invention, there is provided a computer implemented method for determining brain shift by analysing images of the brain, the method comprising the steps of
  (i) taking a first image of the brain of a subject, the first image showing the position of blood vessels in the brain relative to a reference position,
  (ii) taking a second image of the brain that was acquired following an intervention on the subject, the second image having been acquired by Computed Tomography (CT) imaging apparatus and showing the position of blood vessels in the brain relative to the reference position, and
  (iii) calculating brain shift from the shift in position of the blood vessels in at least one region of interest of the brain, with respect to the reference position, between the first and second images.

The present invention thus comprises a computer implemented method for establishing brain shift from first and second images of the brain of a subject. These images show the position of blood vessels in the brain of the subject relative to a certain reference position before and after an intervention. The second image of the brain is acquired using CT imaging apparatus (e.g. intra-operative CT Angiogram imaging apparatus) and can thus be assumed to provide a spatially accurate representation of brain anatomy. In particular, the use of CT imaging apparatus provides accurate spatial information about regions deep within the brain. The images may show the whole brain or just a selected part of the brain. The method comprises assessing the movement of the blood vessels relative to a fixed reference position (e.g. the skull or a point in a common coordinate system) between the first and second images thereby allowing the amount of brain shift to be quantified. The amount of blood vessel movement may be established using all, or preferably just some, of the blood vessels present in the first and second images. As explained below, step (iii) may comprise directly calculating brain shift (e.g. establishing a vector or scalar brain shift value) or indirectly determining brain shift (e.g. by establishing a correction or adjustment to a coordinate system in which positions within the brain are defined or by modifying one or more target positions and/or trajectories within such a coordinate system).

The method of the present invention has the advantage that it can be performed completely in-theatre (e.g. using first and second CT angiogram images acquired using intra-operative CT apparatus) in order to provide a measure of brain shift at one or more locations within the brain at one or more instances during a neurosurgical procedure. Such a measure of brain shift may be used to aid the surgeon when targeting structures in the brain (e.g. by allowing the settings of manual stereotactic apparatus to be adjusted) or to update the target coordinates of a surgical robot system. In this manner, targeting accuracy and hence treatment efficacy can be improved. Alternatively, a pre-operatively acquired first image may be compared to an intra-operatively (or post-operatively) acquired second image.

Advantageously, step (iii) comprises using a co-registration process to determine the shift in position of blood vessels in said at least one region of interest. In other words, a co-registration procedure is performed to find a transformation that best maps blood vessels (in said at least one region of interest) from the first image onto the second image, or vice versa.

Preferably, such a registration procedure is performed using an intensity based registration technique. The registration procedure may comprise a non-linear registration process. Such a non-linear registration procedure may comprise a non-deformable registration procedure. The non-deformable registration procedure may comprise an affine registration process.

Preferably, the registration procedure comprises a rigid registration procedure. Such a rigid registration procedure may comprise using a rigid transformation in which one image is translated, rotated and/or scaled to find the best correspondence between the blood vessels present in said at least one region of interest. In a preferred embodiment, the second image may be left unaltered and the first image may be at least one of translated, rotated and scaled to find the best correspondence. The use of a rigid registration procedure is particularly preferred when both the first and second images are acquired using CT imaging apparatus; the images can then be assumed to be spatially accurate (e.g. substantially distortion-free). As a common reference position is defined in both the first and second image, the transformation provides a measure of blood vessel movement (and hence brain shift) in the region of interest.

Step (iii) may comprise determining brain shift in one region of interest in the brain. Alternatively, step (iii) may comprise establishing brain shift for a plurality of regions of interest in the brain. If a plurality of regions of interest are used, such regions may be overlapping or mutually exclusive. Brain shift may be determined in region(s) of interest in the vicinity of a target site or sites within the brain and/or in region(s) of interest along a trajectory or trajectories through the brain to reach such a target site or sites. A region of interest may comprise a deep brain target. It is preferred that the volume of each region of interest within the brain is smaller than the volume of the whole brain. Preferably, the volume of each region of interest is no larger than 50% of the entire brain volume, more preferably no larger than 25% of the entire brain volume and more preferably no larger than 10% of the entire brain volume. In absolute terms, each region of interest is preferably less than 200 cm$^3$, less than 100 cm$^3$ and more preferably less than 50 cm$^3$. Using such a sub-region of the brain as a region of interest ensures that localised brain shift is determined in that region without being affected by other regions of the brain (e.g. near the skull) where blood vessel movement may be substantially less. This is especially advantageous when establishing brain shift for deep targets, where the amount of brain shift may be markedly different to that present near the cortical surface.

The blood vessels visible in the first and second images may comprise arteries and/or veins. Although the majority of arteries in the brain move with the brain tissue through which they pass, it should be noted that certain veins may exhibit less movement; e.g. peripheral veins may be anchored, to some extent, to the inside of the skull. It is therefore advantageous, but by no means essential, that the first and second images show blood vessels consisting of arteries. It is also preferred, but not essential, that any regions of interest exclude areas of the brain that include blood vessels (such as peripheral veins that are immobilised to some extent relative to the skull) that tend not to move with brain tissue.

Conveniently, the reference position common to both the first and second images is established using a reference structure that is visible in those images. In such a case, two registration processes may be performed. A first registration process may be performed to establish a first transformation between the reference structure visible in each image. This first registration process may be based on a comparison of the whole of the first and second images, or a comparison of a selected portion of those images where the reference structure is visible. A second registration process may then be performed to establish a second transformation between the blood vessels that are present in the selected regions of interest of each image. The difference between the first and second transformations can then provide a measure of brain shift (as evidenced by blood vessel movement) relative to the reference structure.

Any suitable reference structure may be used that is visible in the first and second images. Advantageously, the reference structure comprises an anatomical feature of the subject that has a substantially invariant position within the body. For example, the anatomical feature may comprise the skull, or a portion of the skull, of the subject. Alternatively, the reference structure may comprise a fiducial marker set that is immobilised relative to the skull of the subject. For example, a fiducial marker set may be attached (e.g. screwed or glued) to the skull bone.

Instead of providing a reference structure that is visible in the images, the first and second images of the brain may be acquired by the same imaging apparatus with the head of the subject placed in the same, fixed, location relative to said imaging apparatus. In such an embodiment, the reference position may comprise a positional reference point or origin of said imaging apparatus. In other words, the reference position may be an internal origin or some known reference point defined by the imaging system of the imaging apparatus.

As outlined above, the imaging apparatus used to acquire the second image comprises computerised/computed tomography (CT) imaging apparatus, such as x-ray computed tomography (CT) imaging apparatus. The imaging apparatus used to acquire the first image may comprise any suitable medical imaging apparatus. For example, it may comprise a tomograph, computed tomography (CT), x-ray computed tomography, x-ray, magnetic resonance imaging (MRI), positron emission tomography (PET), ultrasound etc. Preferably, the medical imaging apparatus provides a three dimensional or volumetric image or such a volumetric image can be constructed from data collected using that apparatus. Different imaging apparatus, including different types of imaging apparatus, may be used to collect the first and second images. Preferably, the same imaging apparatus is used to collect the first and second images. In a preferred embodiment, in-theatre computerised tomography angiogram (CTA) imaging apparatus is used to acquire the first and second images. In such an example, the first and second images comprise first and second CTA images, Such CTA apparatus may conveniently comprise a CT scanner device that can be used in-theatre, such as an O-arm (Registered Trade Mark) surgical (CT) imaging system as sold by Medtronics, Inc. The use of in-theatre medical imaging apparatus has the advantage of allowing the first and second images that are analysed using the method of the present invention to be collected whilst the patient is undergoing a surgical procedure. Brain shift measurements can thus be performed quickly (e.g. in seconds or minutes) and the results used to help a surgeon optimise subsequent surgical actions.

Advantageously, the method comprises the step of defining at least a first target site in the first image. This step may, for example, comprise a surgeon reviewing the first image and identifying where one or more neurosurgical instruments (e.g. catheters, electrodes etc) need to be placed. The site or sites identified by the surgeon can then be defined directly on the first image; e.g. a point may be (electronically) marked at a certain position on the first image. A plurality of such target sites may be defined as necessary.

Advantageously, the first target site (and any additional target sites) may be defined in the first image by importing target information from at least one further image. The further image may be taken using further imaging apparatus; this may be a different type of imaging apparatus than that used to acquire the first and second images. The step of mapping target(s) onto the first image from the further image is preferably performed using a registration technique (e.g. of the type described above).

Conveniently, the further image comprises an image acquired using an MRI scanner. Advantageously, the further image shows blood vessels within the brain.

A number of different MRI acquisition protocols may be used to acquire MR images in which blood vessels are visible. For example, magnetic resonance angiography (MRA) allows the blood flowing through vessels to be distinguished from stationary tissue. Blood vessels can also be seen on "T1" MRI scans and the contrast of such images can optionally be improved by injecting a contrast agent into the patient's blood stream (providing a so-called contrast MRA image). The registration procedure may then be based on the comparison (e.g. registration) of blood vessels visible in the first image and the further image. Preferably, the registration process is performed using data showing at least one region of interest within the brain. Such a region of interest may be a volume surrounding a certain target site or volume of interest and may be the same, or different, to the region of interest used when comparing the first and second images.

Advantageously, the co-registration process described above provides the necessary positional link or transformation that allows positions to be mapped between the further image and the first image. The further image itself may be used by the surgeon to identify target sites or trajectories for instruments that are to be inserted into the brain of the subject. Alternatively, target information may be imported from analysis of one or more other images that have a known positional relationship with respect to the further image. For example, the step of co-registering the first image with a further image advantageously permits a surgical planning image (or a plurality of such surgical planning images) also acquired using the further imaging apparatus (i.e. the apparatus used to acquire the further image used in the registration process) to be registered with the first image. The surgical planning image may include a target or targets identified by a neurosurgeon or by using appropriate planning software. Such a surgical planning image may, for example, comprise a pre-operatively acquired image (e.g. taken using MRI apparatus operating in a T2 acquisition mode to show relevant brain structures) that a surgical team have had time to analyse in great detail over the course of several days or weeks.

Although any suitable medical imaging apparatus may be used, it is preferred that the further image comprises an angiogram taken using further apparatus that comprises an MRI scanner. Advantageously, the surgical planning image is acquired pre-operatively using the same MRI scanner (e.g. operating in T2 mode). The subject may be maintained in the same location within the MRI scanner when the further image and the surgical planning image are acquired. In this manner, positions in the further image will correspond to positions in the surgical planning image. If necessary, MR visible fiducials may be used during MR image acquisition to allow all the acquired MRI images to be tied to a common reference position; this can also account for any movement of the subject between scans. As MRI data can be subject to distortions, it also possible for the registration procedure used to generate the transformation between the further (MRI) image and the first image to be elastic. The further (MRI) image may then be morphed (i.e. stretched/squashed and not just translated/rotated) to achieve the best fit with the first image. In this manner, the effects of MRI distortions on targeting accuracy can be reduced or substantially removed. Alternatively, a rigid registration procedure may be used.

The second image analysed using the method of the present invention is acquired after an intervention on the patient. The intervention that occurred may comprise any event or interaction with the subject that may cause the brain to shift within the skull. The intervention may comprise a surgical intervention (e.g. cutting or inserting an instrument into the brain of the subject) or a non-surgical intervention (e.g. re-orientating the subject). It should be noted that a surgical intervention does not comprise a part of the method of the first aspect of the present invention described herein. Advantageously, the second image (i.e. as defined in step (ii)) has been acquired after an intervention that comprises inserting a neurosurgical instrument to said first target site. The second image may thus show the inserted neurosurgical instrument. The intervention may also have comprised inserting further neurosurgical instruments to further target sites. Step (iii) may then further comprise the step of assessing the location of the inserted neurosurgical instrument relative to the first target site. In addition to measuring brain shift, this also allows any positioning errors (e.g. related to unexpected instrument deflections etc.) to be measured.

Step (iii) may comprise directly or indirectly establishing brain shift. For example, step (iii) may comprise directly determining brain shift by calculating a scalar quantity that defines the magnitude of brain shift. Advantageously, step (iii) comprises directly determining brain shift by calculating a brain shift vector that describes both the magnitude and direction (e.g. with respect to the reference position) of brain shift. The brain shift determined in step (iii) may advantageously be used to update target coordinates, for example as used by a surgical robot or a stereotactic system. Step (iii) may alternatively comprise indirectly establishing brain shift. For example, step (iii) may comprise calculating new or updated target coordinates that take into account brain shift or establishing an offset to a co-ordinate system to account for brain shift. Again, such indirect measures of brain shift may be advantageously used for providing target coordinates (e.g. of a surgical robot or a stereotactic system) in which the effects of brain shift have been taken into account. It should also be noted that the ability to compensate for the effect of brain shift during a surgical procedure is particularly advantageous.

It should be noted that the term "image" is used herein to refer to data collected from imaging apparatus (e.g. from a volumetric medical imager or tomograph) and does not mean that such data must be somehow displayed visually. Similarly, references to structures being "visible" in images is intended to mean that information relating to such structures is present in an image and the term visible should not be read as requiring such images or structures to be displayed graphically. The phrase "taking an image" is intended to mean herein retrieving an image that has been acquired (e.g. by loading the image into a computer) and/or acquiring the image using appropriate imaging apparatus.

The above described method is implemented using a computer. The present invention therefore also encompasses a computer that is programmed to implement the above method. Computer software that, when run on a suitable computer, implements the above method is also envisaged. Apparatus including a processor configured to implement the above described method is also encompassed by the present invention.

Apparatus for measuring brain shift is also described herein, the apparatus comprising: means for taking a first image of the brain of a subject, the first image showing the position of blood vessels in the brain relative to a reference position, means for taking a second image of the brain acquired following an intervention on the subject, the second image showing the position of blood vessels in the brain relative to the reference position, and means for determining brain shift from the shift in position of the blood vessels in at least one region of interest of the brain, with respect to the reference position, between the first and second images. The apparatus may include any of the features described above in respect of the associated method. The apparatus for measuring brain shift may be used in combination with a surgical robot, the target coordinates and/or coordinate system used by the surgical robot being updated to account for the brain shift as determined by the means for determining brain shift.

A surgical robot system is also described herein that comprises; a robot for guiding a surgical instrument to at least one target site located within the brain parenchyma of a subject, a medical imaging apparatus (e.g. CT imaging apparatus) for imaging at least a part of the head of a subject, the medical imaging apparatus being suitable for collecting a series of images of the head that show the blood vessels within the brain parenchyma, and a computer controller for updating the co-ordinates of said at least one target site as used by the robot to account for brain shift, said brain shift being determined from a plurality of the images acquired by the medical imaging apparatus.

A further aspect of the invention provides apparatus for performing robotic neurosurgery on a patient. The apparatus preferably comprises a motorised neurosurgical robot for moving a medical instrument to positions defined in a robot coordinate system. The robot may be computer controlled.

The apparatus advantageously also provides imaging apparatus for acquiring intra-operative images of the brain of a patient. For example, the apparatus may include CT imaging apparatus (e.g. an O-arm). At least one position in each intra-operative image is preferably known in the robot coordinate system. For example, a map or link is preferably provided between the robot coordinate system and the co-ordinates of the intra-operative images.

Targeting apparatus is also provided for calculating a target location within the patient's brain to which the medical instrument is to be advanced. The targeting apparatus preferably takes at least one previously (e.g. pre-operatively) acquired image of the patient in which a target has been identified and calculates the corresponding target location in the robot coordinate system by registering said at least one previously acquired image with at least one intra-operative image taken using the imaging apparatus. The at least one previously acquired image may have been acquired pre-operatively (e.g. using MRI apparatus) or at an earlier point in the surgical procedure (e.g. by the imaging apparatus used to acquire the intra-operative image). In a preferred embodiment, the targeting apparatus registers the at least one previously acquired image with the at least one intra-operative image using blood vessels visible in the images. Blood vessels in a certain region of interest may be registered, as described in detail herein, to provide the target location in the robot coordinate system.

There is also described herein a method for registering CT and MRI images, the method comprising the steps of: (a) taking a first image of the brain of a subject acquired using CT apparatus, the first image showing the position of blood vessels in the brain, (b) taking a second image of the brain acquired using MRI apparatus, the second image showing the position of blood vessels in the brain and (c) registering the first and second images using the blood vessels that are visible therein. Any of the above described registration techniques may be used in step (c). For example, a rigid registration may be used. Preferably, the step (c) of registering the first and second images comprises elastically distorting the second image so as to overlay blood vessels visible in the second image on the corresponding blood vessels visible in the first image. Such an elastic distortion of the second (MRI) image removes any distortions that are inherently present in images acquired using such MRI apparatus. Conveniently, the step (c) of registering the first and second images comprises performing a registration in at least one region of interest within the first and second images. Preferably, the volume of each region of interest is no larger than 50% of the entire brain volume, more preferably no larger than 25% of the entire brain volume and more preferably no larger than 10% of the entire brain volume. Targets defined in the MRI coordinate system may then be mapped into the CT coordinate system.

Also described herein is surgical apparatus that comprises: a surgical robot for performing surgery on a patient, the surgical robot comprising an articulated arm having a known position in a robot coordinate system, and medical imaging apparatus for acquiring intra-operative images of the patient, positions in the images acquired by the medical imaging apparatus being defined in an imaging coordinate system, wherein the surgical apparatus comprises a fiducial marker unit that can be held by the articulated arm such that is has a known position in the robot coordinate system, the fiducial marker unit including a reference structure that is visible in images acquired by the medical imaging apparatus. In this manner, the positional relationship between the coordinate systems of the robot and medical imaging apparatus can be found without needing to directly attach (e.g. screw) a fiducial marker to the skull of the patient. This removes the need for minor surgery to attach markers or frames to the skull of the patient prior to performance of the neurosurgical procedure. Preferably, the fiducial marker unit is provided in the form of a tool that can be retained in a tool holder of the articulated arm of the surgical robot. Preferably, the fiducial marker unit can be attached to the articulated arm in a repeatable position (e.g. using a kinematic or pseudo-kinematic attachment mechanism).

There is also described herein a method for determining brain shift, the method comprising the steps of: (i) taking a first image of the brain of a subject, the first image showing the position of blood vessels in the brain relative to a reference position, (ii) taking a second image of the brain acquired following an intervention on the subject, the second image showing the position of blood vessels in the brain relative to the reference position, and (iii) determining brain shift from the shift in position of the blood vessels in at least one region of interest of the brain, with respect to the reference position, between the first and second images. The method may also include any one or more of the steps or features described herein.

The present invention will now be described, by way of example only, with reference to the accompanying drawings in which.

The present invention, which relates to a method of measuring brain shift, will now be described in the context of surgical procedures that could introduce such a brain shift. It should be noted that the computer implemented method for analysing images that is described herein is related to analysing the medical images taken during such a surgical procedure and is not intended to include any of the surgical steps outlined below. These surgical steps are described below purely to aid understanding of how the computer implemented analysis method of the present invention can be used.

Figure 1:
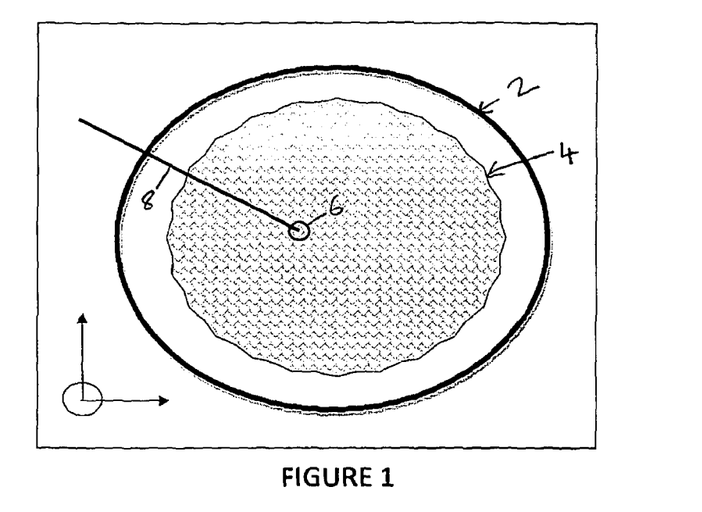
FIG. 1 illustrates pre-operatively acquired MRI (T2) data.

Referring to FIG. 1, a pre-operatively acquired (T2) MRI image is illustrated in very general terms. The image shows the skull 2 and brain 4 of a patient. Such a T2 MRI image would also show in detail the different structures within the brain, although such structures are omitted from FIG. 1 for ease of understanding.

As is traditional in the art of neurosurgery, such an MRI image is used by surgeons to plan surgical procedures and is usually acquired pre-operatively (e.g. days or weeks in advance). One example of a surgical procedure that may be planned using such an MRI image is the placement of a catheter to deliver a therapeutic agent to a specific structure within the brain. FIG. 1 also illustrates a target region or target site 6 and the trajectory 8 along which a catheter is to be inserted to reach the target located at the identified brain structure; these are typically planned manually by the neurosurgeon. Positions within the image shown in FIG. 1 are defined in an MRI co-ordinate system. Such an MRI co-ordinate system may, for example, be defined with reference to MR visible fiducial markers that are secured to the patient head prior to imaging (but not shown in FIG. 1).

Figure 2:
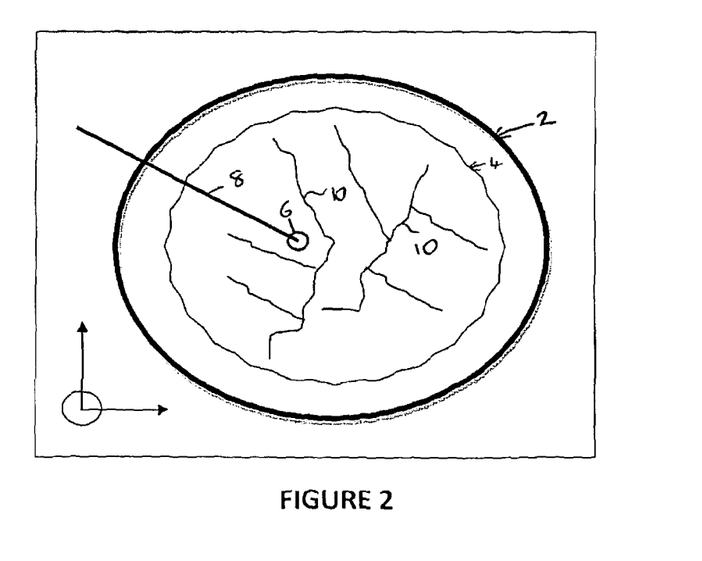
FIG. 2 illustrates pre-operatively acquired MRA data.

Referring next to FIG. 2, there is shown an illustration of a (T1) MRI image taken after an MRI contrast agent has been injected into the patient's blood stream. This image, which can be referred to as a contrast MR angiogram or "contrast MRA" image, shows the various blood vessels 10 within the brain but it does not show in any detail the various structures within the brain; this image is therefore typically unsuitable for target identification and detailed surgical planning purposes. It should be noted that, instead of a contrast MRA, a standard MRA (in which the flow of blood within vessels is distinguished from the stationary tissue surrounding those vessels) could be acquired.

The contrast MRA image shown in FIG. 2 is of the same patient as the MRI image of FIG. 1 and all positions are described in the same MRI co-ordinate system. This may be achieved, for example, by reference to MR visible fiducial markers that have a fixed position relative to the skull. Alternatively, the patient's head may be maintained in the same position between scans thereby removing the need for fiducial markers. The acquisition of the contrast MRA image in the same co-ordinate system as the MRI image allows the target site 6 and trajectory 8 from the MRI image shown in FIG. 1 to be mapped onto the contrast MRA image of FIG. 2 in which the blood vessels are visible.

Figure 3:
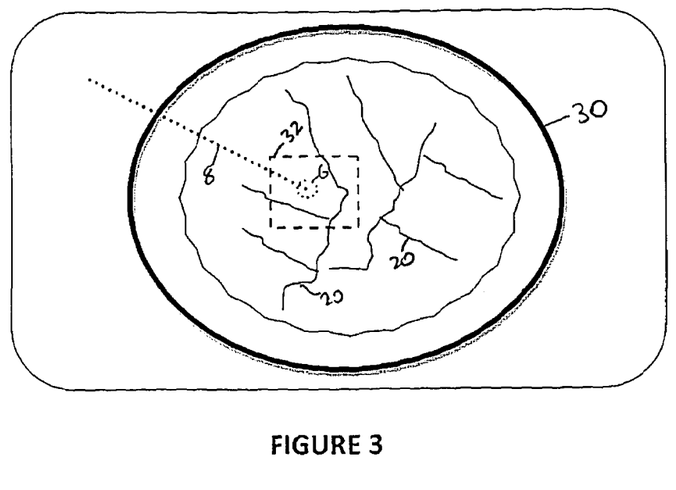
FIG. 3 illustrates a CT angiogram acquired with the patient "in-theatre" prior to neurosurgery.

Referring to FIG. 3, there is shown a first CT angiogram (CTA) image of the patient. This CTA image is acquired using in-theatre CT apparatus (which is preferable mobile) whilst the patient is located on the operating table with their head secured to that table in the desired position for the subsequent neurosurgical procedure. The first CTA image, which is acquired after the injection of a suitable CT contrast agent into the patient's bloodstream, shows the location of the blood vessels 20 within the brain in the CT co-ordinate system. In this example, the CT co-ordinate system is defined relative to a reference structure in the form of the skull 30 that is also visible in the first CTA image.

A registration procedure is then performed to register the contrast MRA image of FIG. 2 (which includes the target site and trajectory information) with the first CTA image of FIG. 3. This registration process involves defining a region of interest 32 around the target site 6 and then performing a co-registration process to find the best positional match between the CTA and contrast MRA images in this region of interest. This registration process is preferably intensity based and makes use of the blood vessels that are visible in both the CTA and contrast MRA images. To account for MRI distortions, the registration process may be fully or partly elastic to allow the contrast MRA image to be morphed (compressed/stretched) to fit the vessel structure of the CTA image. Further details of the preferred co-registration procedure are outlined in more detail below, but the basic result is a mathematical transformation that allows positions measured in the MRI co-ordinate system to be mapped into the CT co-ordinate system. This registration process therefore allows the target site 6 and trajectory 8 that were defined in the MR co-ordinate system to be mapped into the CT co-ordinate system, as shown in FIG. 3.

The above described process thus permits target and trajectory information that is based on pre-operatively acquired MRI data to be mapped into the CT co-ordinate system that is established "in-theatre" on the day of surgery. Importantly, this can be done without the need for fiducial markers to remain affixed to the patient between the pre-operative MRI scans and the surgical procedure. As will be described in more detail below, the CT co-ordinate system may also be linked to a robotic or stereotactic coordinate system that allows external equipment, such a stereotactic frame or a surgical robot, to insert surgical instruments to desired targets within the brain that have been described in CT based co-ordinates.

Figure 4:
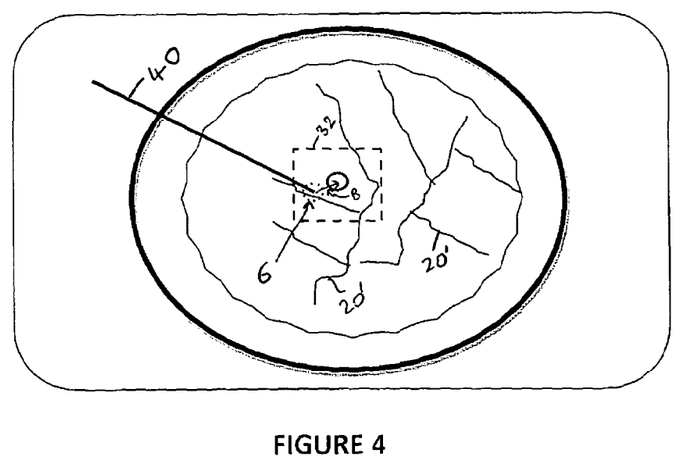
FIG. 4 illustrates a CT angiogram acquired with the patient in-theatre after a catheter has been surgically implanted.

Referring to FIG. 4, a second CTA image is schematically illustrated that is taken after insertion of a catheter 40. This second CTA image is taken with the same in-theatre CT apparatus that was used to acquire the first CTA image of FIG. 3 and with the patient's head still secured to the operating table (noting some head movement may have occurred during surgery). As can be seen from FIG. 4, the catheter has been accurately inserted along the trajectory shown in FIG. 3 and has its tip precisely located at the target co-ordinates that were defined using the first CTA image shown in FIG. 3. The brain has, however, shifted relative to the skull at some point during the surgical procedure (noting that this brain shift is greatly exaggerated in FIG. 4). This brain shift (which results in the blood vessels adopting the positions shown as 20' in FIG. 4) means that the tip of the catheter is not actually placed at the target site within the brain where delivery of the therapeutic agent is required. In other words, there has been brain shift defined by the vector B shown in FIG. 4 that has caused the tip of the catheter to deviate from its desired target within the brain parenchyma.

It should be noted that in FIG. 4 it is assumed that the catheter is located precisely where it was originally intended and that all the error arises from brain shift. It is, of course, possible that there may be some other error in catheter placement or that the catheter may deflect away from the desired trajectory due to variations in the density of brain tissue. In such a case, it is also possible to establish from the second CTA image any variation in the actual catheter position from the position that was planned.

Normally, brain shift of the type described above would only be identified post-operatively (e.g. during a subsequent MRI scan) or when the treatment failed. The acquisition of a second CTA image, however, permits any brain shift to be measured perioperatively in the following manner. Firstly, a registration procedure is performed to establish a reference transformation that describes the spatial relationship between the skull (or one or more predefined regions of the skull) shown in the first and second CTA images. The first CTA image is then registered with the second CTA in the region of interest 32 of the brain that surrounds the target site; this provides a brain (blood vessel) transformation. The difference between the reference transformation and the brain (blood vessel) transformation describes how much the region of interest 32 within the brain has moved relative to the skull between the first and second CTA images. In other words, a vector describing brain shift in the region of interest 32 can be established using the skull as a fixed position reference feature.

This manner of measuring brain shift can be used purely as a tool to quantify the amount of brain shift that accompanies a certain neurosurgical procedure. If the brain shift exceeds a certain amount, the procedure may be reversed (e.g. by explanting a catheter) and performed again (e.g. by implanting a catheter to the shifted target site). Alternatively, brain shift may be measured multiple times during a surgical procedure and if any significant brain shift is measured an appropriate correction to the target co-ordinates may be applied. For example, brain shift could be measured after boring an opening the skull and piercing the dura. The measured brain shift could then be used to update the target co-ordinates that are to be used during a subsequent stereotactic or robotic procedure to insert a neurosurgical instrument. Measurement of brain shift using the above method could also be performed periodically during the implantation of a neurosurgical instrument, and the target coordinates or the origin of the surgical coordinate system updated accordingly.

Figure 5:
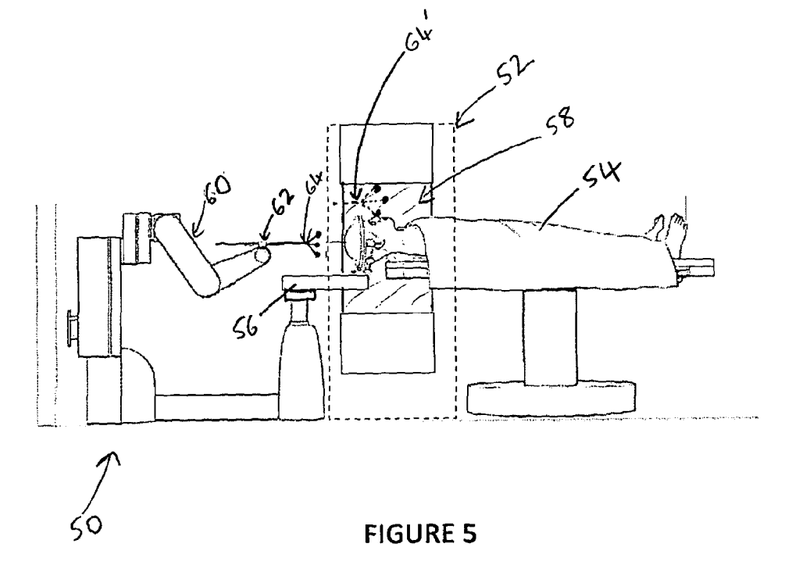
FIG. 5 shows a surgical robot and an in-theatre CT scanner.

A technique will now be described with reference to FIG. 5 for relating the coordinate system of a neurosurgical stereotactic robot, such a Neurolmate robot system 50 produced by Renishaw Mayfield, to the coordinate system of an associated CT apparatus 52. In particular, FIG. 5 shows a Neurolmate robot system 50 arranged to perform surgery on a patient 54 whose head is held rigidly in place on a table 56 linked to the robot 50. A mobile, in-theatre, CT scanner 52 is located around the patient's head and arranged to acquire a CT image in a CT imaging volume 58 that encompasses the head. The robot system 50 also comprises an articulated robotic arm 60 having a mount 62 at its distal end to which neurosurgical instruments and the like can be attached. In FIG. 5, the articulated arm 60 carries a CT visible marker arrangement 64 that has a known (pre-calibrated) position relative to the mount 62; i.e. the CT visible marker arrangement 64 has a known position within the robot coordinate system.

In order to establish a positional link between the robot coordinate system and the CT coordinate system, the articulated arm 60 places the CT visible marker arrangement 64 in the CT imaging volume 58 and the mobile CT scanner 52 performs a CT scan. A suitable position for the CT visible marker arrangement 64 during such a scan is shown as 64' in FIG. 5. The resulting CT image (which may be a CT angiogram image as described above) thus shows positions within the patients head (e.g. positions of blood vessels and target sites) relative to the CT visible marker arrangement 64. Analysis of the CT image thus allows a link or transformation to be established between the CT coordinate system and the robot coordinate system, thereby allowing target positions and trajectories that have been defined in the CT coordinate system (which may have been mapped into the CT coordinate system from an MRI coordinate system as described above) to be mapped into the robot coordinate system. The marker arrangement 64 may then be detached from the mount and replaced with a surgical instrument that can be guided along the desired trajectory to the target coordinates. The marker arrangement 64 may be re-attached to the mount (in the same position) and re-imaged as often as required; for example, if the map between the CT coordinate system and the robot coordinate system needs to be re-established or verified.

It should be noted that it is also possible to establish the map between the CT coordinate system and the robot coordinate system prior to the patient being present. For example, the CT visible marker arrangement could be held by the arm of the robot in various different locations within the imaging volume of the CT scanner prior to the patient being placed on the table 56. This does, however, assume that the relative position of the CT scanner and surgical robot does not change when the patient is introduced. Alternatively, the patient 54 could have the CT visible marker arrangement affixed to their skull, for example as part of a head frame or by direct (e.g. screw thread) attachment. Such an attachment may comprise a feature to engage with an instrument held by the arm 60 of the robot 50 to enable the position of the CT visible marker to be established in the robot coordinate system.

Once the transformation between the CT coordinate system and the robot coordinate system has been established, it is possible to update target positions defined in the robot coordinate system if those target positions alter (e.g. due to brain shift). For example, the amount of brain shift may be measured in the manner described above (i.e. by looking for such brain shift relative to the skull). Assuming the patient's skull does not move with respect to the robot, the measured brain shift may then be directly used to correct the target coordinates in the robot coordinate system. It should be noted that, because brain shift is measured relative to the skull in the above described method, the CT scanner may be moved relative to the patient between measurements. Furthermore, such corrections for brain shift may be determined periodically or at certain points in the procedure. The target position(s) in the robot coordinate system can then be changed accordingly during the procedure to account for any brain shift. It should also be noted that the origin of the robot coordinate system may be adjusted to account for brain shift; this has the same effect as altering the target positions.

Although the above examples refer to assessing the brain shift in the region of a target, it should be noted that brain shift may be measured for a plurality of regions of interest within the brain. These regions of interest may correspond to multiple target sites (e.g. if implanting a plurality of neurosurgical instruments) and/or multiple points along an insertion trajectory (e.g. to ensure the inserted instrument does not damage sensitive tissue or puncture any large blood vessels). It is also important to note that although the above examples show two-dimensional images, these are merely slices through three-dimensional or volumetric images. The two-dimensional illustrations described above are simply provided for ease of understanding and the skilled person would fully appreciate that, in most practical situations, the coordinate systems and any brain shift would be defined and measured in three-dimensions.

The registration of images is described above in general terms, but more details of suitable registration processes will now be described with reference to FIGS. 6 to 8.

The co-registration of two data sets that show blood vessels (e.g. Angio-MR, Angio-CT, vessel models or vessel atlas data sets) can be performed using a variety of known registration techniques. For example, suitable registration methods include any one of the following three groups of techniques. Firstly, it is possible to use intensity based registration methods. If the 3D vessels data comprises a vessel model or atlas, it is preferably converted into 3D volume data prior to registration. In such techniques, the transformation is determined by maximising the intensity similarity. Secondly, it is possible to use feature based registration methods. These methods typically extract certain features from both data sets. Suitable features may include vessels junction and/or vessels shapes. The optimum transformation can be estimated by minimising the distance between identified features of the different sets. Finally, hybrid techniques based on both intensity and feature registration methods can be used. Such hybrid methods include the so-called active appearance model and particle system methods.

Figure 6:
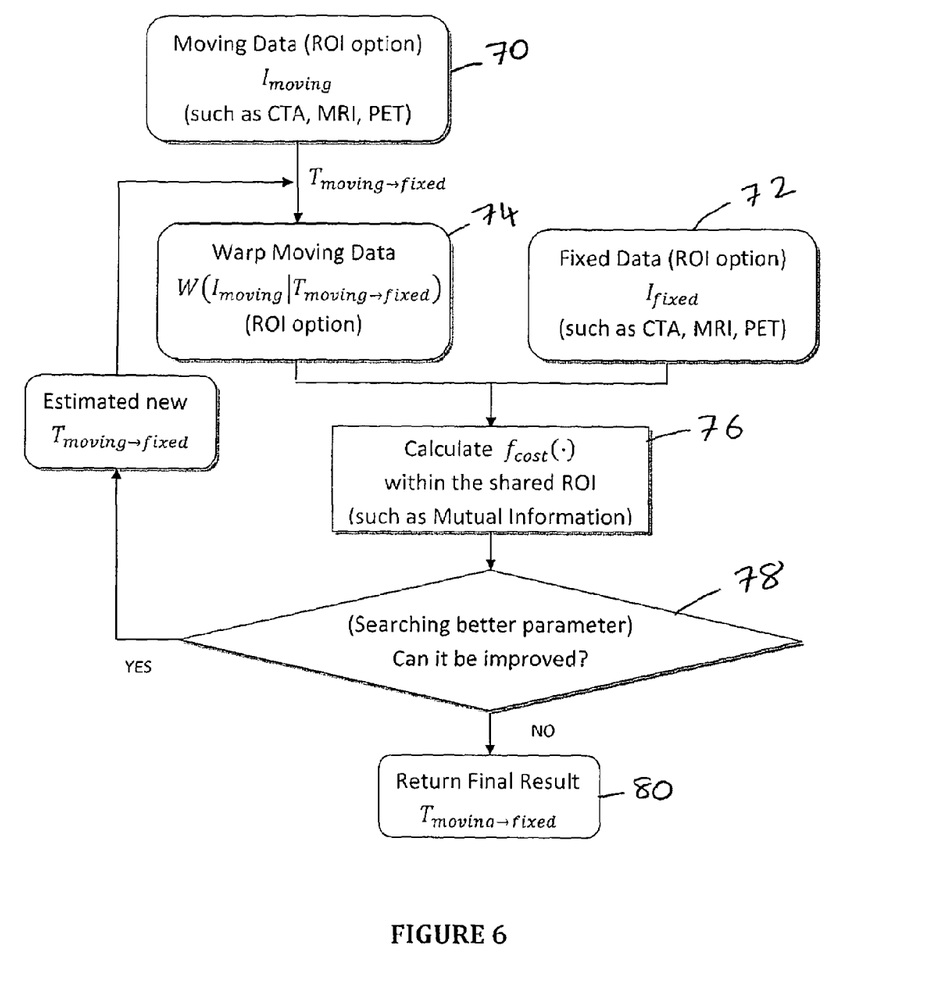
FIG. 6 is a flow chart outlining a suitable registration process.

Referring now to FIG. 6, a flow chart for an intensity based registration process is shown. As can be seen from FIG. 6, step 70 comprises taking so called moving data (such as the second CTA image mentioned above) and step 72 comprises taking fixed data (such as the first CTA image mentioned above). A region of interest is defined for the fixed and moving data, such as a small region surrounding a target site defined in the brain. A step 74 is performed which warps the moving data (in the region of interest) using a transform ($T_{moving\text{-}fixed}$). The intensities of the warped moving data and fixed data are compared in step 76 by calculation of a cost function. A step 78 then attempts to select improved parameters for the values used in the transform ($T_{moving\text{-}fixed}$) which are fed back into step 74. This process is iteratively repeated until the correlation between the warped moving data and the fixed data can be improved no further. The final, optimised, value of the transform ($T_{moving\text{-}fixed}$) is then returned in step 80.

This registration process can also be viewed as a superposition of two basic parts. The first part is the selection of the transformation model and the second part is the estimation of the transformation parameters. Moreover, most image registration problems can be treated as optimisation problems that can be described in general mathematical terms as follows:

$$\arg\max_{T_{moving \to fixed}} (f_{cost}(I_{fixed}, W(I_{moving} | T_{moving \to fixed}))), \quad (1)$$

where $l_{moving}$ and $l_{fixed}$ are the moving (to be warped) and fixed (target) data, $T_{moving\text{-}fixed}$ is a parameter vector in the selected transformation model, $W(l_{moving}|T_{moving\text{-}fixed}})$ is warped moving data under the transformation model with the parameter $T_{moving\text{-}fixed}$, and $f_{cost}(\cdot)$ is a cost function to measure the intensity similarity between the warped moving data and the fixed data.

Figure 7:
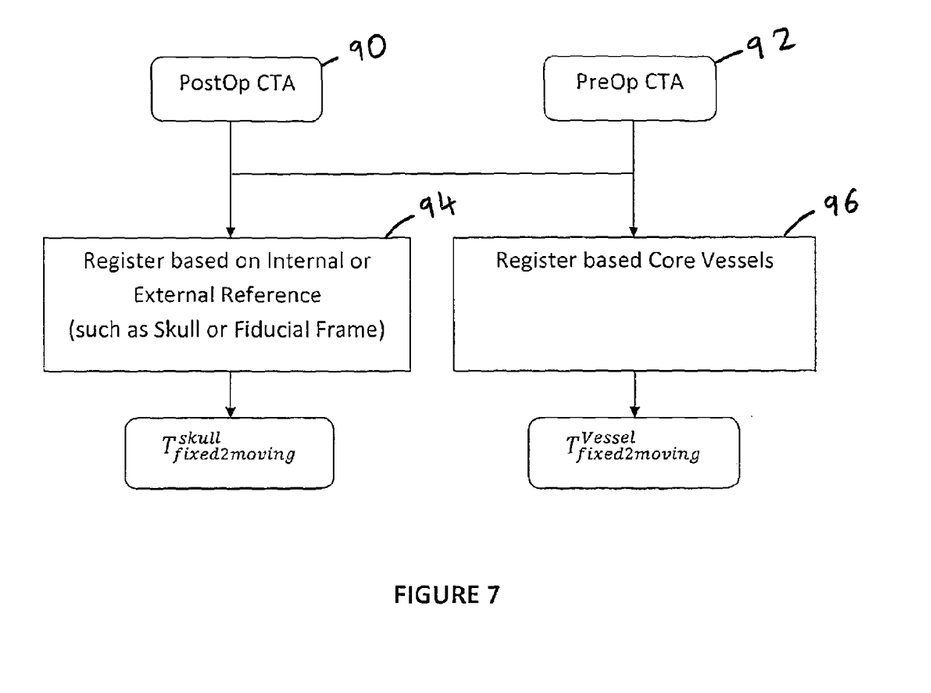
FIG. 7 is a flow chart s outlining a process for the registration of pre-operative and post-operative CT data.

Referring next to FIG. 7, a flow-chart describing the use of a registration technique to measure brain shift between pre-operative and post-operative CTA images is shown. The registration technique uses two region based rigid registrations (3 translations and 3 rotation angles) using the pre-operative and post-operative CTA data. The method thus estimates the brain shift by measuring the spatial changes with respect to the skull at the point where the brain shift is to be measured (e.g. at the tip of a stylette). This gives a vector indicating the magnitude and direction of brain shift with respect to the skull. The registration is based on the volumetric CTA data and it minimises slice distance and slice thickness issues. As it is CT based, it also avoids any MRI distortion.

Referring to FIG. 7 in more detail, steps 90 and 92 comprise taking pre-operative and post-operative CTA images respectively. Both images show a reference structure (e.g. the skull) and blood vessels within the brain. A step 94 is performed that comprises a rigid registration between the pre-operative and post-operative CTA images based on the reference structure (e.g. the skull); this produces the transformation $T_{fixed2moving}^{skull}$. A step 96 is also performed that comprises co-registering the blood vessels in a predefined region of interest in the pre-operative and post-operative CTA images; this produces the transformation $T_{fixed2moving}^{vessel}$. The size of this region of interest may, for example, be 50×40×15 mm.

Brain shift is then calculated, as follows, at two points where the tips of two stylettes (left and right stylettes) are located after insertion. Firstly, the tip position of each stylette is determined in the and post-operative CTA image in the UVW coordinates of the CT machine; these positions are defined as (a) $r_{fixed}$ and (b) $l_{fixed}$. The positions of the stylette tips are then calculated in the pre-operative CTA using the $T_{fixed2moving}^{skull}$ transform thereby giving the positions (a) $r_{moving}^{skull}$ and (b) $l_{moving}^{skull}$. The positions of the stylette tips are then calculated in the pre-operative CTA using $T_{fixed2moving}^{vessel}$, which provides the positions (a) $r_{moving}^{vessel}$ and (b) $l_{moving}^{vessel}$.

This allows the brain shift ($S_l$ and $S_r$) at the position of each stylette to be calculated from the expressions:

$$S_l = r_{moving}^{skull} - r_{moving}^{vessel} \quad (2a)$$

$$S_r = l_{moving}^{skull} - l_{moving}^{vessel} \quad (2b)$$

Figure 8:
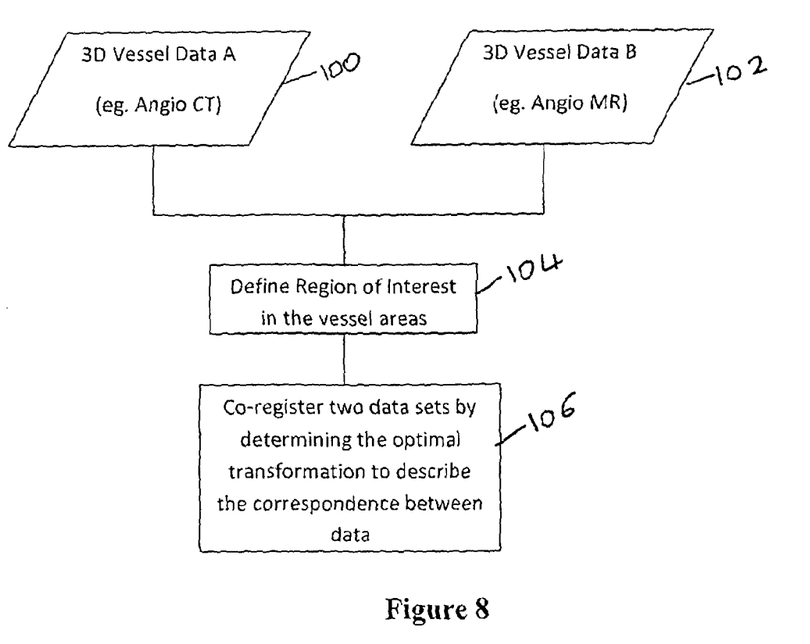
FIG. 8 is a flow chart outlining a process for the registration of MRA and CTA data.

Referring to FIG. 8, a process for registering MRA data with CTA data is illustrated. Steps 100 and 102 comprise taking (e.g. retrieving or acquiring) CTA data and MRA data respectively. A step 104 is then performed of defining a region of interest in an area where blood vessels are visible. This region of interest may be located around a target structure or site within the brain to which a neurosurgical instrument is to be inserted. A step 106 is then performed to co-register the two (MRA and CTA) data sets by determining the optimal transformation to describe the correspondence between the data. Information from the MRA data (e.g. relating to the position of target structures) can then be mapped onto the CTA data.

The techniques described above are preferably implemented using an appropriately programmed computer. It should also be remembered that the above examples are non-limiting and provided merely to aid understanding of the invention. The skilled person would be fully aware of the many variations to the above examples that would be possible in accordance with the general teachings that are outlined above.

The invention claimed is:

1. A computer implemented method for determining brain shift by analysing images of the brain, comprising the steps of:
   (i) taking a first image of the brain of a subject, the first image showing the position of blood vessels in the brain relative to a reference position,
   (ii) taking a second image of the brain that was acquired after an intervention on the subject, the second image having been acquired by Computed Tomography (CT) imaging apparatus and showing the position of blood vessels in the brain relative to the reference position, and
   (iii) calculating brain shift from a shift in position of the blood vessels in at least one region of interest of the brain, with respect to the reference position, between the first and second images and calculating a brain shift correction based on the calculated brain shift and updating the position targeted by a surgical robot based on the calculated brain shift correction.

2. A method according to claim 1, wherein step (iii) comprises using a co-registration process to determine the shift in position of blood vessels in said at least one region of interest.

3. A method according to claim 1, wherein the reference position is established from a reference structure that is visible in the first and second images.

4. A method according to claim 3, wherein the reference structure comprises an anatomical feature of the subject, such as a portion of the skull, that has an invariant position within the subject's body.

5. A method according to claim 3, wherein the reference structure comprises a fiducial marker set that is immobilised relative to the skull of the subject.

6. A method according to claim 1, wherein the first and second images of the brain have both been acquired by the same CT imaging apparatus with the head of the subject placed in the same, fixed, location relative to said CT imaging apparatus, wherein the reference position comprises a positional reference point or origin of said CT imaging apparatus.

7. A method according to claim 1, wherein the computed tomography CT) imaging apparatus comprises in-theatre computed tomography angiogram (CTA) imaging apparatus.

8. A method according to claim 1, comprising the step of defining at least a first target site in the first image.

9. A method according to claim 8, comprising the step of registering the first image with a further image acquired using further imaging apparatus, wherein the further image also shows blood vessels in the brain and the registration procedure is based on the comparison of blood vessels in a region of interest.

10. A method according to claim 9, wherein the step of registering the first image with a further image permits a surgical planning image acquired using the further imaging apparatus to be registered with the first image, the surgical planning image comprising a target as identified by a neurosurgeon.

11. A method according to claim 10 wherein the further image comprises an MR angiogram and the further imaging apparatus comprises an MRI scanner.

12. A method according to claim 11, wherein the surgical planning image is acquired pre-operatively using the MRI scanner.

13. A method according to claim 8, wherein the second image is acquired after an intervention that comprises inserting a neurosurgical instrument to said first target site, the second image showing the inserted neurosurgical instrument.

14. A method according to claim 1, wherein step (iii) comprises calculating a brain shift vector that describes the magnitude and direction of brain shift with respect to the reference position.

15. A computer implemented method for determining brain shift by analysing images of the brain, comprising the steps of:
   (i) taking a first image of the brain of a subject, the first image showing the position of blood vessels in the brain relative to a reference position,
   (ii) taking a second image of the brain that was acquired after an intervention on the subject, the second image having been acquired by Computed Tomography (CT) imaging apparatus and showing the position of blood vessels in the brain relative to the reference position, and
   (iii) calculating brain shift from a shift in position of the blood vessels in at least one region of interest of the brain, with respect to the reference position, between the first and second images and calculating a brain shift correction based on the calculated brain shift and updating the position targeted by a stereotactic system based on the calculated brain shift correction.

* * * * *